(12) United States Patent
Sjogren et al.

(10) Patent No.: US 8,187,618 B2
(45) Date of Patent: May 29, 2012

(54) SUSTAINED RELEASE MICROBIAL INSECT CONTROL COMPOSITION AND MEANS

(75) Inventors: Robert D. Sjogren, Ladera Ranch, CA (US); David R. Sjogren, Sherwood, OR (US)

(73) Assignee: B2E Micobials LLC, Sag Harbor, NY (US)

( * ) Notice: Subject to any disclaimer, the term of this patent is extended or adjusted under 35 U.S.C. 154(b) by 0 days.

(21) Appl. No.: 12/916,866

(22) Filed: Nov. 1, 2010

(65) Prior Publication Data

US 2011/0045043 A1 Feb. 24, 2011

Related U.S. Application Data

(62) Division of application No. 11/115,033, filed on Apr. 25, 2005, now Pat. No. 7,837,988.

(51) Int. Cl.
*A01N 63/02* (2006.01)
*A01N 25/08* (2006.01)
*A01P 7/00* (2006.01)
*A01P 7/04* (2006.01)

(52) U.S. Cl. ................ 424/409; 424/93.461; 424/93.46

(58) Field of Classification Search .............. None
See application file for complete search history.

(56) References Cited

U.S. PATENT DOCUMENTS

| 4,631,857 A | | 12/1986 | Kase et al. | |
|---|---|---|---|---|
| 4,732,762 A | * | 3/1988 | Sjogren | 424/409 |
| 4,971,796 A | * | 11/1990 | Sjogren | 424/417 |
| 5,484,600 A | * | 1/1996 | Sjogren | 424/405 |
| 6,337,078 B1 | * | 1/2002 | Levy | 424/406 |
| 2006/0239977 A1 | | 10/2006 | Sjogren et al. | |

* cited by examiner

*Primary Examiner* — Shanon A Foley
(74) *Attorney, Agent, or Firm* — Pauly, DeVries Smith & Deffner, L.L.C.

(57) ABSTRACT

Effective sustained release of microbial pesticides in aquatic environments can be achieved by the combination of buoyant particles with a particulate microbial active ingredient. The resulting materials in the form of a particulate have combined density of less than one. The materials are then dispersed into gypsum slurry that is poured into briquette molds, or made into granules or pellets of various sizes, to form a solid, sinking, pest control composition. Once applied in aquatic field sites, the surface of the matrix slowly dissolves, releasing many minute buoyant pesticide laden particles to the water surface over the life of the product. Once at the surface, the particulate microbial pesticide(s) release from the buoyant particles and are distributed throughout the water column to be ingested by susceptible immature filter feeding mosquitoes and pestiferous flies.

7 Claims, 7 Drawing Sheets

SUSTAINED RELEASE MICROBIAL INSECT CONTROL COMPOSITION AND MEANS

CROSS-REFERENCE TO RELATED APPLICATION

This application is a divisional of application Ser. No. 11/115,033, filed Apr. 25, 2005, which issued as U.S. Pat. No. 7,837,988 on Nov. 23, 2010, the entire disclosure of which is incorporated herein by reference.

FIELD OF THE INVENTION

The invention relates to a microbial pesticidal sustained release composition, treatment unit and means for the control of pestiferous insects. The treatment unit can be distributed in aquatic environments to provide long lasting effective pest control. The unit contacts water at the surface and sinks to the bottom of the aquatic environment. When in contact with water, the pest control unit and means releases pesticide materials after sinking, providing desired low level pesticide concentrations, to achieve effective pest control over prolonged time periods.

BACKGROUND OF THE INVENTION

Mosquitoes and biting flies develop worldwide in aquatic environments during temperate months, creating serious public health problems through disease transmission and biting insect annoyance. Control of these public health insects is costly due to the significant labor, equipment and material requirement necessary. To achieve control, all potential breeding sites within the pest insect's flight range must be inspected weekly during summer months, and if found breeding, control materials must be applied. The development of effective, soluble pesticide controlled release formulations for aquatic environments lasting up to 150 days in the early 1980's by Sjogren (U.S. Pat. No. 4,732,762) provided significant labor savings and reduced control costs. This technology has been commercialized using the soluble insect growth regulator S-Methoprene, and has gained widespread acceptance and use.

In the mid 1980's, a microbial pathogen *Bacillus thuringiensis israelensis* (Bti) was discovered and subsequently commercialized for pest control. In the mid 1990's, a second microbial pathogen of mosquitoes, *Bacillus sphericus* (Bsph) was also brought to market. These microbial pesticides are highly selective for small immature biting flies (Nematocera), are recognized for their environmental compatibility, and have become control materials of choice for use in mosquito control programs. To be effective these microbial pathogen particles (>1.0 specific gravity) must be applied to the water surface and ingested by aquatic immature biting fly stages, before they settle out of the water column. This is now achieved for short term control by liquid or floating corn cob granules (<½ mesh) applied to flooded field sites that contain mosquito larvae. The duration of control achieved by such liquid or granular treatments vary with the dosage applied, ranging from 24 to 72 hours with Bti, and 7 to 28 days with Bsph.

In 1996, Sjogren (U.S. Pat. No. 5,484,600) described a timed-release microbial granule formulation in the form of a composite particle. The particle is in the form of a dense core, a flotation particle, a pesticide and an adhesive that delivered microbial pesticidal particles to the water surface for mosquito control. In that invention, microbial powders were blended with a buoyant agent and attached to the outside of a sinking granular carrier. A slow dissolving, water soluble protein binder released the buoyant agent and microbial pesticide to the water surface over 10 to 30 days.

Kase (U.S. Pat. No. 4,631,857) describes the delivery of particulate (1.5 to 15 micron) microbial pesticide consisting of a mixture of cork, a larvicidal micro-organism (Bti), gypsum plaster and water sufficient to set the plaster to produce a floating molded unit. When applied into small aquatic field sites, the plaster slowly dissolves releasing the Bti at the water surface. Although the composition is reported to control mosquitoes for up to one month in very small field sites, the invention has a number of disadvantages that are overcome by the present invention. They are: 1) the floating molded unit releases Bti directly into the water as the plaster disintegrates, which limits the lateral dispersal of the sinking particulate pesticide; 2) the floating unit can be beached by winds rendering it ineffective, and anchoring it in place is labor intensive; 3) the unit's relatively large size, about 2 inches diameter, and its light weight, renders it impractical to disperse with mechanical equipment; and 4) its control effectiveness is limited to approximately 30 days.

Particulate pest control compositions used in water perform best when they are evenly distributed in field mosquito breeding sites, and remain in place after application, delivering particulate pathogenic particles at the water surface in their vicinity. Floating compositions readily drift away from where they are applied, and do not achieve the uniform distribution of microbial particles at the water surface in large sites, required for pest insect feeding ingestion. Thus, sinking compositions perform more dependably than floating compositions under diverse field conditions.

The development of an effective sinking sustained release microbial composition which delivers particulate, non-water soluble, microbial pesticides at the water surface over a prolonged period to control aquatic biting flies, is difficult to achieve. For microbial particulate pesticides to be effective they must be uniformly distributed on the water surface of field sites and remain available long enough to be ingested by filter feeding mosquito larvae. Granule and pellet compositions must be small enough in size to permit large numbers to be distributed with mechanical equipment to provide multiple release loci. For such small units to be effective, the composition must be highly efficient to continuously deliver pest controlling quantities of particulate pesticides.

Accordingly, a substantial need exists for a sinking sustained controlled release microbial pesticide composition that remain in place when applied, achieve effective microbial control of pest populations, that provides a continuous release of microbial pesticide to the water surface to maintains an effective mosquito controlling concentration for long periods during the temperate or breeding season.

BRIEF DISCUSSION OF THE INVENTION

I have found a composition comprised of a microbial pesticide and a matrix is an efficient long term (>30 days) means of achieving mosquito control when applied uniformly to field mosquito breeding sites. Such a matrix can include a buoyant agent, aqueous slurry of microbial pesticide and means to form a matrix. The pesticide slurry can be loaded onto the buoyant agent to produce a microbial pesticide component. Such loaded buoyant particles have a specific gravity of <1.0, after which the resulting particles are dried and reduced in size back to discrete particles by grinding, can be blended with a plaster or gypsum cement slurry and cast into molds to set. The molded unit is an efficient long-term means of achieving mosquito control when applied uniformly to field mosquito breeding sites.

No water-soluble adhesives are used. A gypsum briquette is used as the controlled release mechanism, into which buoyant particles are loaded with microbial insecticide and incorporated to form a heaver than water briquette invention that can easily be tossed into water bodies at regular intervals, or applied in pellet form by hand or mechanical means. Upon application, such articles effectively penetrate vegetation canopies, sink to the bottom of water bodies and stay in place over time, slowly and continually releasing very large numbers of individually loaded microbial insecticide particles to the water surface with the consistency and uniformity necessary to provide dependable control.

The present invention overcomes the limitations of floating compositions by use of a sinking composition that: 1) remains in place at the bottom of an aquatic environment, when applied in field sites, thus providing uniformly spaced release loci; 2) slowly releases many buoyant (<1.0 specific gravity) particles each loaded with particulate microbial pesticide, each of which transports the microbial particles to the water surface. Once pesticidal laden particles release to the surface they disperse throughout the site, aggregating and slowly releasing their payload in protected areas where target larval insect stages aggregate and feed; 3) can be made into a) pellets and/or granules that can be mechanically distributed in the environment, and b) briquettes of various sizes for hand application to field sites on equidistant intervals. Field trials have demonstrated the present invention controls for >60 days with pellets (Mulla, 2003) and >150 days with briquettes as small as 12 grams (Su, 2003). The pest control agent comprises a microbial agent comprising one or more of a bacterium, a fungus, a virus, or a combination or mixture thereof. The particulate pest control agent comprises an insecticide which is present in the total composition at an amount of about 20 wt-% or less. The microbial insecticide can be a mosquito control agent and can use *Bacillus thuringiensis israelensis* alone, *Bacillus sphericus* alone, both *Bacillus thuringiensis israelensis* and *Bacillus sphericus* microbial control agents in combination. Genetically modified forms and or combinations of these strains can be used. The unit of the invention can be made up in a plaster composition. A preferred plaster has a high compressive strength that ranges from about 2,000 to about 15,000 pounds per square inch or from about 4,000 to 14,000 pounds per square inch. The pest control agent can be present in the total composition in an amount of about 2 to about 15 wt-percent and the plaster in an amount about 30 to 90 wt-%. The term particulate or particle means a small unit of millimeter size ranging up to a larger unit of substantial mass that can be mechanically or manually distributed.

In the case of Bti products, the typical bioassay does not measure the concentration of anything in particular, but rather evaluates overall potency, or killing power against the intended target. The Basic Insecticide Bioassay, by dosing the insects, avoids most of the factors such as formulation, application method, organic matter, and palatability that might influence how much toxicant gets to the insect. With most toxicants, there is a regular relationship between the toxicant dose and the percentage of insects that are affected. The characteristics of the relationship for any given toxicant and insect species can be learned by dosing groups of the insects with different amounts of the toxicant to develop a dose-response curve. All doses (or more properly, concentrations) below 0.4 mg/ml killed no larvae. All concentrations above 1.4 mg/ml killed all of the larvae. In between these two concentrations, along the response curve, are concentrations that will kill some fraction of the test insects. Approximately 0.77 mg/ml will typically kill about one half an insect population. Every Bti bioassay must include the simultaneous bioassay of a reference standard against the same group of test insects. A reference standard is a preparation of the same type of Bti with an established potency.

DETAILED DISCUSSION OF THE INVENTION

The pest control unit of the invention typically is in the form of a solid regular or irregular shape that can be distributed into the environment. The material must be mechanically stable such that the forces of production, bagging, storage, transportation and distribution into the environment does not substantially reduce the unit or particle size or change the geometry of the unit. The unit can have virtually any regular or irregular shape. The unit can have an irregular or agglomerated shape with no significant symmetry and have a irregular surface and structure. A preferred form of the unit of the invention is a regular geometric shape. Such shapes include a variety of well known geometric shapes including briquette, a pillow, a sphere, a generic prism, a pyramid, oval, cylinder, truncated cylinder, cube, rectangular prism, triangular prism and others. The shapes can have a surface area that ranges from about 10 to about 50,000 mm$^2$, preferably about 2,000 to 30,000 mm$^2$ and often 2,500 to about 7,500 mm$^2$. The major dimension of such a unit ranges from about 1 millimeter size up to as large as 10 cm in major dimension. The unit can be shaped to permit easy grip and throw if distributed individually. The solid pest control unit comprising an effective amount of a particulate microbial pest control agent can use an effective slow release amount of a plaster having a high compressive strength of at least 500 lbs. per square inch, and a hardening amount of water. The unit is sufficiently hard to be distributed over large areas by mechanical means. The unit has a surface area of about 10 to about 50,000 mm$^2$, when immersed in an aqueous pest breeding site can provide an effective amount of the pest control agent, and when dry does not release the agent. The unit can be a cylinder having dimensions of about 1 to 100 millimeters in diameter and about 1 to 100 millimeters in height. The unit can have a regular shape is as a truncated cone having dimensions of about 20 to 45 millimeters on the major diameter, about 15 to 35 millimeters on the minor diameter, and about 15 to 40 millimeters in height. The truncated cone is about 35 to 40 millimeters in the major diameter, about 30 to 35 millimeters in the minor diameter, and about 30 to 35 millimeters in height. The surface area of such a solid pest control unit is about 4,000 to 7,000 mm$^2$ and wherein the mass of the solid pest control means is about 3 to 45 or about 0.2 to 100 grams. The unit can include a buoyancy agent (about 0.1 to 20 wt. %) that can regulate the specific gravity to a desired level from about 0.85 to about 1.15 depending on the needs of the user. The materials are then dispersed into gypsum slurry that is poured into briquette molds, or made into granules or pellets of various sizes, to form a solid, sinking, pest control composition. Once applied in aquatic field sites, the surface of the matrix slowly dissolves, releasing many minute buoyant pesticide laden particles to the water surface over the life of the product. Once at the surface, the particulate microbial pesticide release from the buoyant particles and is distributed throughout the water column to be ingested by susceptible immature filter feeding mosquitoes and pestiferous flies.

Control personnel will first inspect and evaluate an aquatic site for pest activity and then can place the pest control unit of the invention into the environment. The pest control unit of the invention can either be manually or mechanically distributed into the aquatic site. The unit of the invention is typically distributed into the aquatic site at a rate of about 1 to about 50 (units) of the microbial pesticide per 10 square meter of the aquatic site for effective pest control activity. To obtain optimal control, the pest control unit is typically distributed over a large portion of the aquatic site; however, the entire site does not have to be uniformly treated with the individual units. As the units contact water in the aqueous site, the microbial pesticide is released at a substantial rate and is distributed by natural effects throughout the aquatic site.

The pest control unit must be applied at least once during a temperate season or during the breeding season to effectively control insects, however, the unit can be reapplied to an aquatic breeding site repeatedly during the breeding season, depending on the amount of microbial pesticide distributed and the lifetime of the unit. The control unit can be used at a rate of one 44 gram briquette per each, 10 $m^2$, 5 $m^2$ or 1 $m^2$.

Microbial Pesticide

The term microbial pesticide as employed here is intended to include any microbial active material used for control of plants, animals or microorganisms, such as mosquitoes, fungi, algae, snails, weeds, including in particular microbial insecticides, microbial biocides, and other microbial materials of economic value for management of terrestrial and aquatic environments. Microbial pesticides include microbes that are pathogen to insect pests that include but are not limited to specific bacterium, fungus and virus materials.

A great variety of microbial pesticides can be used which are compatible with the plaster and buoyant particle composition of the invention. Representative non-limiting examples of the pesticides are: 1) bacteria in the genera: *Agrobacterium, Ampelomyces, Bacillus, Pseudomonas*, and *Streptomyces*, 2) fungi in the genera *Beauveria, Candida, Coelomyces, Coniothyrium, Fusarium, Gliocladium, Metarhizium, Paecilomyces, Pythium, Trichoderma*, and *Verticillium*, and 3) viral agents such as granulosis virus, and nuclear polyhedrosis viral agents.

Preferred microbial pathogens for use in the invention are those that have been found effective as pesticides, or biocides, including bacteria, fungi, and viruses. The literature reports numerous studies on the relative biological activity of such microbial pathogens. They include many species of bacteria, such as *Bacillus thuringiensis*, widely used in the control of agricultural pests, *Bacillus thuringiensis israelensis*, and *Bacillus sphericus* effective for the control of immature flies such as mosquitoes (Culicidae), aquatic midges (Chironomidae), mushroom flies (Sciaridae) etc. Fungal microbials include *Lagenidium gigantium, Coelomyces*, etc. Microbial activity of materials such as the microbial pesticide of the invention is expressed in International Toxic Units (ITU). The normal range of ITUs applied in the field for insect control of the invention control is about 1 lb.-$acre^{-1}$ to 20 lb.-$acre^{-1}$ or about 2 lb.-$acre^{-1}$ to 10 lb.-$acre^{-1}$ of a 200 ITU/mg of unit or at a rate of about 0.1 to 2 gms-$m^{-2}$ or about 0.2 to 1 gms-$m^{-2}$ of a 200 ITU/mg of unit.

Microbial pathogens commercially developed for the control of insects of public health importance include *Bacillus thuringiensis israelensis* (Bti), *Bacillus sphericus* (Bsph) and *Lagenidium gigantium*. Bti introduced commercially in the early 1980's, quickly found commercial acceptance and is now used worldwide in public health insect control programs. Its is widely used because of it's commercial availability, target specificity (i.e. negligible environmental impact), citizen preference as a larval control material of choice, its relatively low cost, rapid direct kill of treated stages, and its effectiveness for the control of most mosquito species. Bti has few disadvantages. They are: 1) the microbial particles must be uniformly distributed throughout treated sites to be ingested (i.e. it is effective only when evenly applied in field sites), and 2) treatments are short lived, thus provide no residual control of subsequent mosquito egg hatches.

*Bacillus sphericus* (Bsph) was introduced commercially in the mid 1990's, for its residual control capability. Applications to underground sites and to highly organic waters are reported to control for two to four weeks at high label application rates. Similarly, Bsph has few disadvantages. They are: 1) like Bti, the requirement that the microbial particles be uniformly distributed in treated sites, and 2) the residual control of subsequent mosquito hatches is short in clean water sites.

Buoyant Agent

Microbial pesticide particles must be released from the water surface and ingested by filter feeding target organisms to be effective. Thus, sinking sustained release pesticide compositions must deliver particulate pesticide particles to the water surface. This invention employs a buoyant agent to deliver said particles to the water surface.

Many different types of buoyant agents with a specific gravity of less than 1.0, about 0.99 to 0.85 may be used in the invention. As not all such materials are known and new ones may be developed in the future, I do not wish to be held to a specific type. Specific gravity is a unitless measure of the density of a material to the density of water at a defined temperature.

Of the materials tested, effective buoyant agents include perlite, and polypropylene powders with and without internal void space, to which microbial insecticides are attached. Particle sizes useful include those in the size range of 1 to 10,000 microns. More preferably, particle sizes in the range of 2 to 2,000 microns may be used. Most preferably, the particle size range is between 10 to 1,000 microns.

Plaster

Sjogren (U.S. Pat. No. 4,732,762) teaches that gypsum dissolves in water and is an effective high density (sinking) slow release matrix for water soluble pesticides. Kase (U.S. Pat. No. 4,631,857) describes the use of plaster in combination with cork and the microbial agent *Bacillus thuringiensis israelensis* (Bti) to create a floating microbial composition. This invention reveals for the first time a unique new sinking microbial pesticide composition that uses gypsum plasters and cements with a buoyant agent loaded with microbial powders to slowly release microbial pesticides to the water surface for mosquito and pestiferous aquatic insect control.

Dehydration of gypsum (calcium sulfate dehydrate ($CaSO_4.2H_2O$) in an open kettle by direct heating in the range of 390-570° F., will result in beta-calcium sulfate hemihydrate, CaSO4.).5H2O, commonly called plaster. Typically, plaster crystals are long, needle-like, irregular in shape and porous. The shape and porosity of the crystalline particles results in high water absorbency. The powder, when mixed with water, will require about 60 parts of water to about 100 parts of plaster to give a "workable" slurry consistency. Plasters can contain a variety of additives that provide properties such as wettability, strength, hardening rate, particle size and low viscosity slurries. Gypsum cement is a preferred embodiment with higher compressive strengths and slower rates of dissolution (Sjogren, U.S. Pat. No. 4,732,762).

Suggested ranges for the units of the invention include:

TABLE 1

| Ingredient | Low Range (wt %) | High Range (wt %) |
| --- | --- | --- |
| Plaster | 20-90 | 30-70 |
| Bti | 0.1-20 | 2-10 |
| Buoyant powder | 1-20 | 2-15 |
| Accelerator | 0-5 | 0.1-4 |
| Water | 15-60 | 15-50 |

Example I

The formula for a representative solid, sinking, *Bacillus thuringiensis israelensis* (Bti), sustained release composition is:

| Ingredient | W/W % |
| --- | --- |
| Plaster of Paris | 50.00 |
| Water | 36.20 |
| Accelerator | 1.00 |
| Bti | 5.00 |
| Floatation (Polypropylene) Powder | 7.80 |

The physical properties of low-density polypropylene powder suitable to use as a buoyant vehicle, include a particle size range of 1 to 10,000 microns, more preferably 5 to 1000 and most preferably 10 to 500 microns. The common polypropylene density ranges from 0.86 to 0.91 gram/cubic centimeter. Suitable densities include any density less than 1.0 capable of being loaded with particulate microbial active ingredient, the combination of which when soaked in water >24 hours demonstrates a specific gravity of less than 1.0.

The composition is prepared by weighing 5 lbs. of the Bti microbial active ingredient to which is added 17 lbs. of de-ionized water. The Bti is then mixed thoroughly to prepare a aqueous slurry. Then 7.8 lbs. of Accurel polypropylene powder is placed in a mixing vessel. The Bti slurry is then added and the combination blended well with a mixer and a vacuum is drawn on the mixture to pull the Bti slurry into the polymer void space. The loaded powder is then dried, and mechanically ground back to the initial size of the polymer powder.

Then 50 lbs. of Plaster of Paris is placed into a mixing vessel with 36.2 lbs. of de-ionized water is added. The plaster is mixed thoroughly with a 1750 rpm mixer for 5 minutes. Then 12.8 lbs. of Bti loaded polymer powder and 1 lb. of plaster accelerator is added to the slurry and blended well. The combined slurry is then placed in briquette molds to shape the final product form, where it sets up into hard units. Once set, the units are discharged from the molds, dried and packaged.

Example II

The formula for a representative solid, sinking, *Bacillus sphericus* (Bsph) sustained release composition is:

| Ingredient | W/W % |
| --- | --- |
| Plaster of Paris | 50.00 |
| Water | 36.20 |
| Accelerator | 1.00 |
| Bsph | 5.00 |
| Accurel Powder | 7.80 |

The composition is prepared by weighing 5 lbs. of the Bsph microbial active ingredient to which is added 17 lbs. of de-ionized water. The Bsph is then mixed thoroughly to prepare an aqueous slurry. Then 7.8 lbs. of Accurel polypropylene powder is placed in a mixing vessel. The Bsph slurry is then added and the combination blended well with a mixer and a vacuum is drawn on the mixture to pull the Bsph slurry into the polymer void space. The loaded powder is then dried, and mechanically ground back to the initial size of the polymer powder.

Then 50 lbs. of Plaster of Paris is placed into a mixing vessel with 36.2 lbs. of deionized water is added. The plaster is mixed thoroughly with a 1750 rpm mixer for 5 minutes. Then 12.8 lbs. of Bsph loaded polymer powder and 1 lb. of plaster accelerator is added to the slurry and blended well. The combined slurry is then placed in briquette molds to shape the final product form, where it sets up into hard units. Once set, the units are discharged from the molds, dried and packaged.

Example III

The formula for a representative solid, sinking, *Bacillus thuringiensis israelensis* (Bti), sustained release composition is:

| Ingredient | W/W % |
| --- | --- |
| Plaster of Paris | 50.00 |
| Water | 36.20 |
| Accelerator | 1.00 |
| Bti | 5.00 |
| Propyltex Powder | 7.80 |

The composition is prepared by weighing 29 lbs. of a Bti microbial active ingredient liquid concentrate. The Bti liquid concentrate is then mixed thoroughly with 7.8 lbs. of Propyltex polypropylene powder in a mixing vessel. The combined slurry is then blended well with a mixer. The loaded powder is then dried, and mechanically ground back to a <100 micron powder.

Then 50 lbs. of Plaster of Paris is placed into a mixing vessel with 36.2 lbs. of de-ionized water is added. The plaster is mixed thoroughly with a 1750 rpm mixer for 5 minutes. Then 12.8 lbs. of Bti loaded polymer powder and 1 lb. of plaster accelerator is added to the slurry and blended well. The combined slurry is then placed in briquette molds to shape the final product form, where it sets up into hard units. Once set, the units are discharged from the molds, dried and packaged.

Example IV

The formula for a representative solid, sinking, combination Bacillus thuringiensis israelensis (Bti) and Bacillus sphericus (Bsph) sustained release composition is:

| Ingredient | W/W % |
| --- | --- |
| Plaster of Paris | 50.00 |
| Water | 36.20 |
| Accelerator | 1.00 |
| Bti | 1.00 |
| Bsph | 4.00 |
| Accurel Powder | 7.80 |

A representative solid, sinking, combined Bti and Bsph sustained release microbial pesticide composition is made by weighing 4 lbs. of the microbial pesticide Bsph and 1 lb. of the microbial pesticide Bsph. The technical powders are then blended, to which is added 17 lbs. of de-ionized water. The Bsph & Bti are then mixed thoroughly with the water to prepare an aqueous slurry. Then 7.8 lbs. of Accurel polypropylene powder is placed in a mixing vessel. The Bsph & Bti slurry is then added and the combination mixed well with a mixer and a vacuum is drawn on the mixture to pull the Bsph slurry into the polymer void space. The loaded powder is then dried, and mechanically ground back to the initial size of the polypropylene powder.

Then 50 lbs. of Plaster of Paris and is placed into a mixing vessel and 37 lbs. of de-ionized water is added. The plaster is mixed thoroughly with 1750 rpm mixer for 5 minutes. The 12.8 lbs. of Bti & Bsph loaded polymer powder and 1 lb. of plaster accelerator is then added to the plaster slurry and blended in. Then the combined slurry is added into molds in the final form of the product, where it sets up into hard units. Once set, the units are discharged from the molds, dried and packaged.

Example V

A 30-40 day controlled release gypsum granule, <6 mesh in size was made as follows. Gypsum prills were placed in a rotary blender (alternatively a sand core) in a prilling drum to form a base. The base particles are then coated with thin slurry of pre-blended high compressive strength gypsum, causing the granules to drag. Then 5 to 100 micron Accurel® polypropylene powder, pre-loaded with Bti (alternatively Bsph) microbial powder was slowly added onto the tacky slurry coated granules. The powder tacks onto the slurry, drying the surface of the granule particles, until the granules run free. Next, a second addition of thin gypsum slurry was added and prilled onto the granules to form a second gypsum layer, then another addition of microbial loaded polypropylene powder was added and tacked onto the slurry until it surface moisture was taken up and granule again free rolls. This process was repeated again and again to build up controlled release gypsum particles containing the particle mass required for application by ground or aerial broadcast application equipment to field mosquito breeding sites. Once applied, in the presence of water the slow dissolution of the gypsum coating slowly releases buoyant microbial pathogen loaded particles to the water surface where the microbial control agents release into the water column to control immature mosquito and fly pests.

Mosquito Control Field Trials

Figure 1:
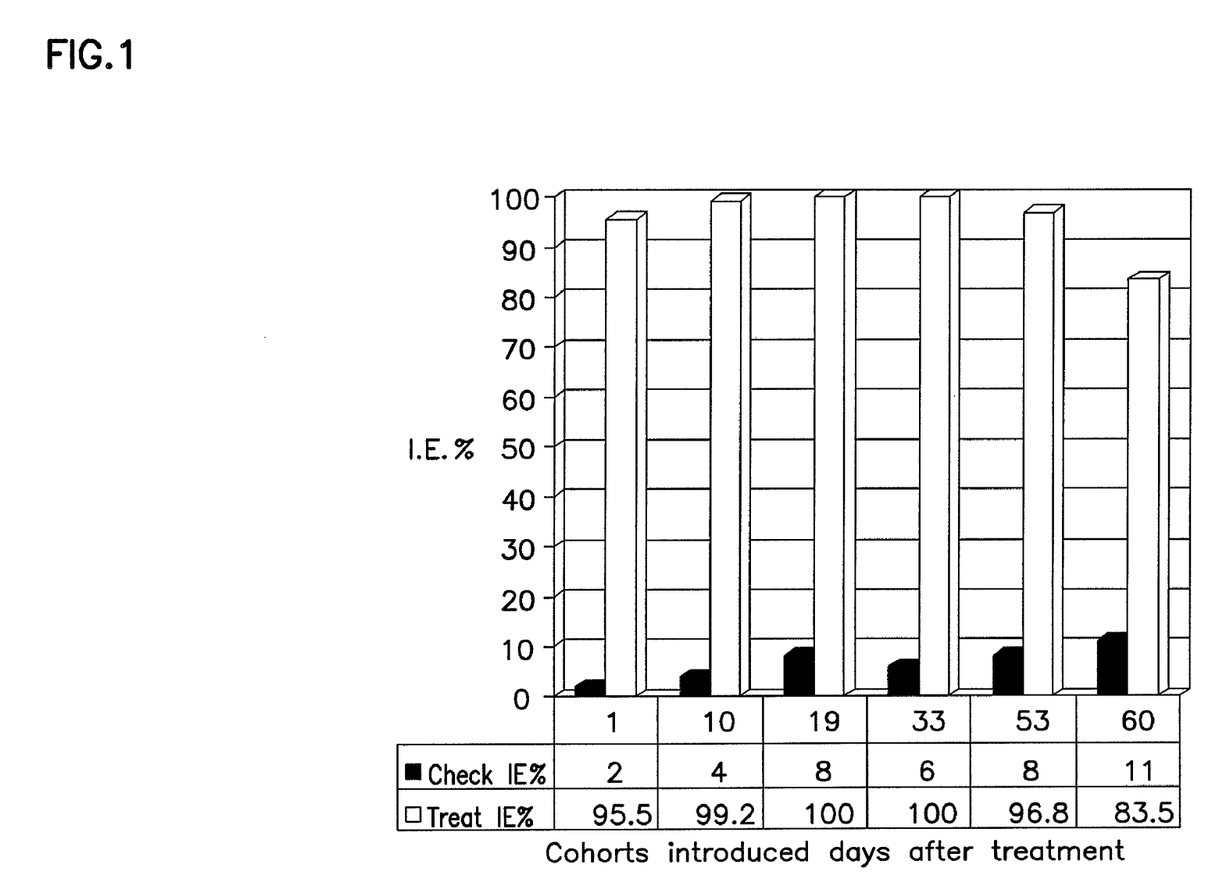
FIGS. 1-5 show the efficacy of the pesticide invention in preventing emergence of certain mosquitoes over a lengthy treatment.

Pellet Trials Against *Aedes aegypti*—Thailand:

Dr. Mir Mulla, Professor, Department of Entomology, University of California, Riverside conducted replicated field trials using 5% Bti, sinking ¼ inch diameter by 3/16 inch pellets in 200 liter earthen domestic water storage jars representative of those that breed the Yellow Fever and Dengue mosquito vector *Aedes aegypti* in Bang Bua Thong, Nonthaburi, Thailand. Ten grams of pellets were added per jar in a randomized block design experiment. Then 25, $3^{rd}$ instar mosquito larvae were added per jar at the start of the experiment and at each interval. Larval survivors were assessed at 48 hours, and pupal skins were counted one week after addition of larvae. When larval development slowed and all larvae not pupated and emerged within a week, pupal skins were counted and removed on two occasions, after one week and again after 2 weeks. Jars were then challenged again with new larvae. FIG. 1, shows the efficacy of Bti gypsum pellets against successive cohorts of *Aedes aegypti* larvae (25 third-instar larvae/jar) in 200 L earthen water storage jars.

Briquet Trials Against *Aedes aeqvpti* and *Culex quinquefasciatus*—California:

Dr. Tianyun Su, Consulting Medical Entomologist, Riverside, Calif. conducted 4.36 square feet, simulated catch basin, microcosms trials to evaluate the effectiveness of 12 gram and 44 gram sinking slow release microbial pesticide briquette compositions, containing 7% Bti in replicated chambers. Rabbit pellets were introduced as larval food, i.e. 15.5 g/tub, every other week. *Culex quinquefasciatus* and *Aedes aegypti*, early $3^{rd}$ instars, were used in bioassays wherein 25 larvae were introduced into floating sentinel cages in each replicate on regular intervals. Results were expressed as percent inhibition of adult emergence, I.E. %. Fifty percent of the water in tubs was replaced with fresh tap water monthly to simulate water dilution in natural catch basins. Residual weight of the briquettes was measured monthly by retrieving the briquettes and calculating dry weight according to a previously determined ratio of wet/dry weight.

The 12 gram briquettes applied at the rate of 1 briquette/tub, inhibited the emergence of adult *Culex quinquefasciatus* mosquitoes by $\geq 85\%$ for 154 days. The 44 gram briquettes applied at the rate of 1 briquette/tub inhibited *Culex quinquefasciatus* mosquito adult emergence $\geq 92\%$ for 154 days, at which time the test was terminated with 1 gm of briquette remaining.

The small briquettes at an application rate of 1 briquette/tub also inhibited the emergence of adult *Aedes aegypti* mosquitoes by $\geq 82\%$ for 154 days. The large briquettes at 1 briquette/tub inhibited *Aedes* adult emergence $\geq 93\%$ for 154 days, when the test was terminated.

Figure 2:
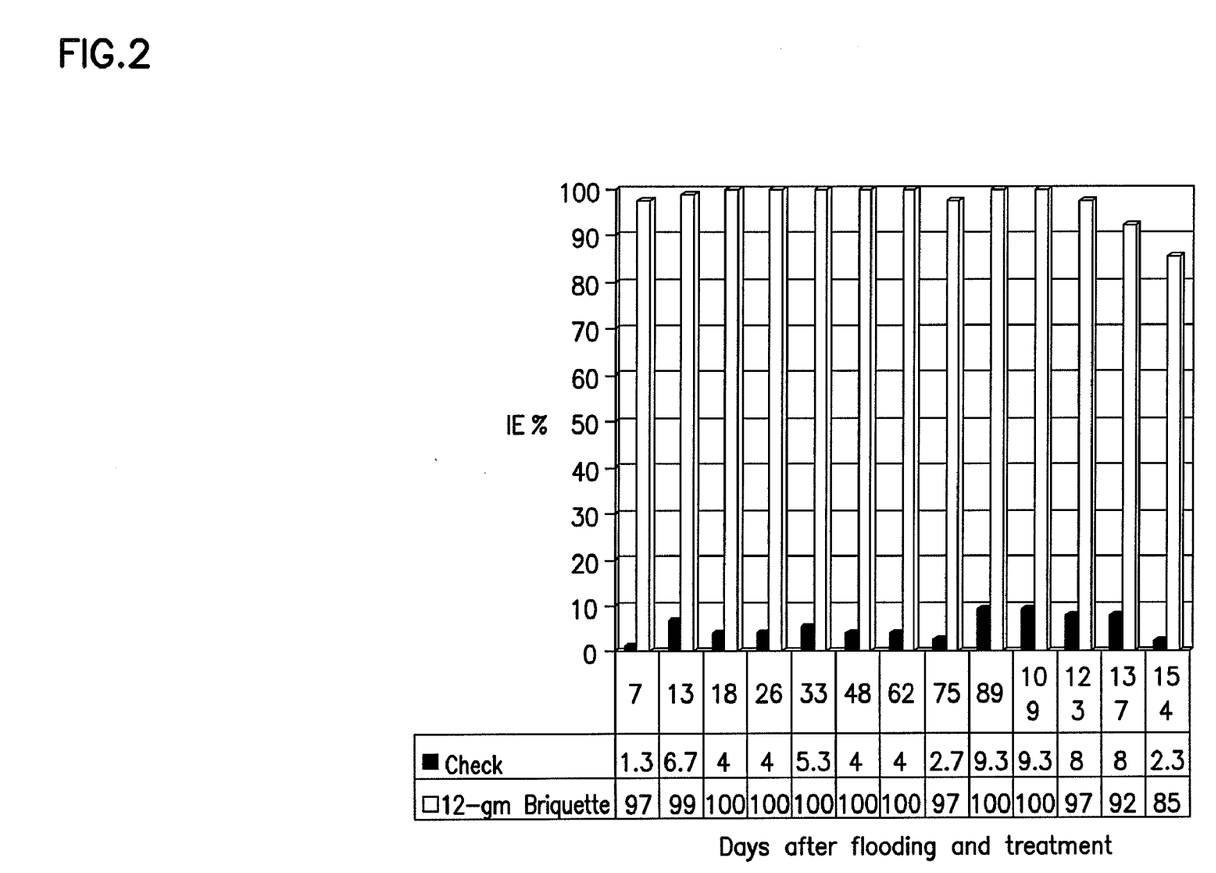

FIG. 2 shows the efficacy of the 12 gram version of the briquette at a rate of 1 briquette per 200 liter jar or tub against Culex q.

Test Methods

The test procedures for the graphics data shown in the figures are as follows. Test materials included Bti pellets applied at 5 lb/ac, 227 mg/tub, and two Bti briquette formulations a 12.5 gm per briquette and a 44 gm briquette. Briquettes were applied at a rate of 1 briquette/tub. The simulated catch basin microcosm habitat environment employed plastic tubs with a surface area of 4.36 square feet. Water depth averaged 6 inches; water volume was approximately 15 gallons. Tubs were set up out of sunlight, under representative catch basin environment conditions. Rabbit pellets were used as larval food at a dose rate of 0.025% calculated on the initial water content, i.e. 15.5 g/tub, every other week. Briquettes using the technology of the invention were used as treatments and were introduced at flooding. Three replicates of each treatment material were used. *Culex* spp (*quinquefasciatus* and *stigmatosoma*) and *Aedes aegypti*, early third instars were used as bioassay organisms. Floating sentinel cages were used to demonstrate that the Bti was released at the water surface, i.e. to prevent larval access to Bti settled out on the bottom of the chambers. Twenty-five larvae were introduced per sentinel cage. About 1 gram of rabbit pellets was put in each cage to insure larval access to sufficient food. Cages were set up weekly for pellets, initially weekly for small briquettes, then every other week; and initially weekly, then every other week, then monthly for large briquettes. Results were expressed as IE %, i.e. percent inhibition of adult emergence. *Culex* cages were read twice a week until all larvae died or pupated and adults emerged. *Aedes aegypti* cages were also read twice a week; pupae were collected and introduced to a screened cage without sugar feeding. Exuviae were counted after all pupae died or emerged. Emerged adults starved to death inside the cage to prevent escape of this exotic species. Half of the water in the tub microcosms was replaced with fresh tap water monthly to simulate water dilution in natural catch basins. The residual weight of the briquettes was measured monthly by retrieving the briquettes gently, draining them, then weighing and calculating the dry weight according to a previously determined wet/dry weight ratio. The water temperature was monitored with a Taylor Maximum-Minimum Thermometer at bottom of a tub at regular intervals.

Figure 3:
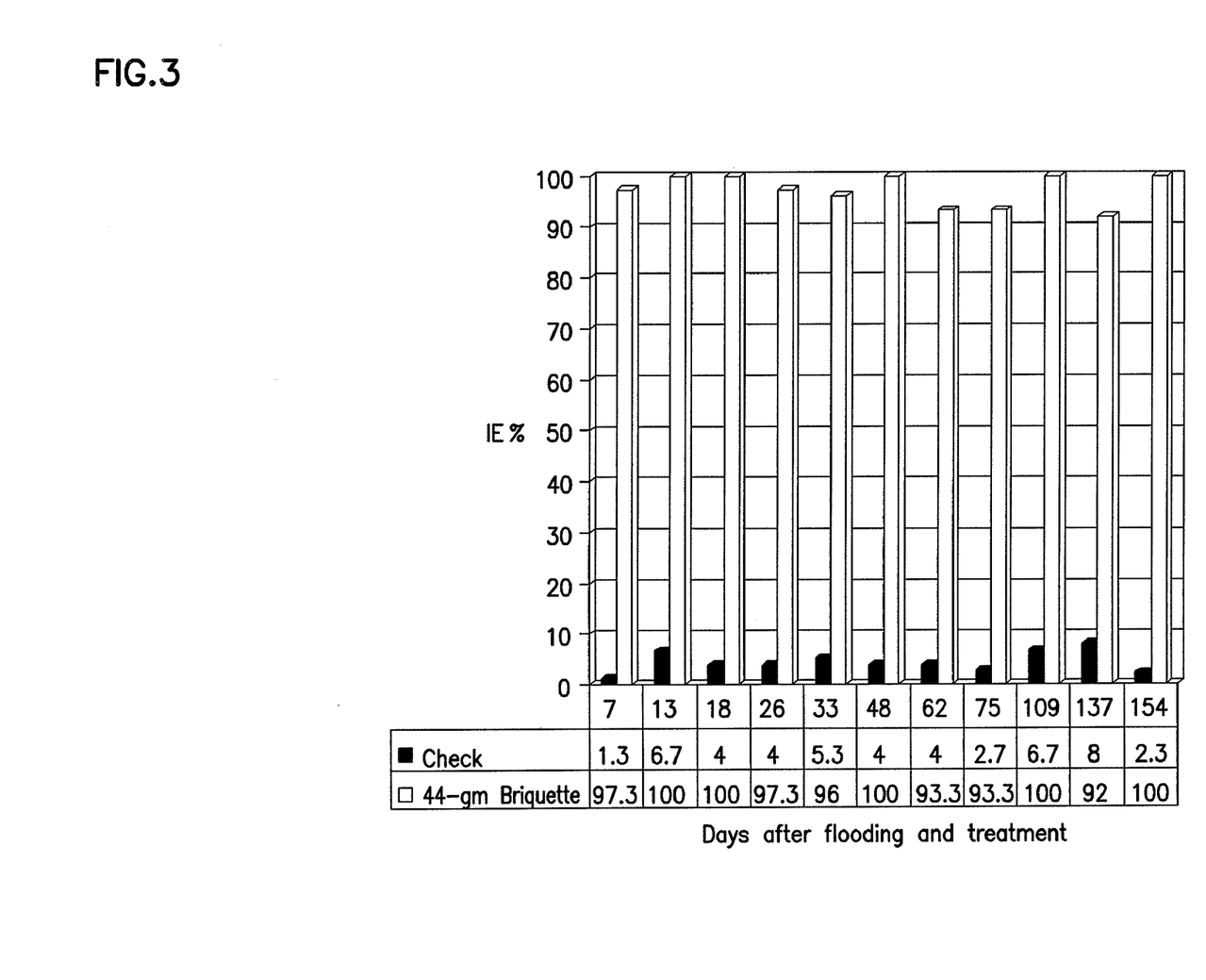
Figure 4:
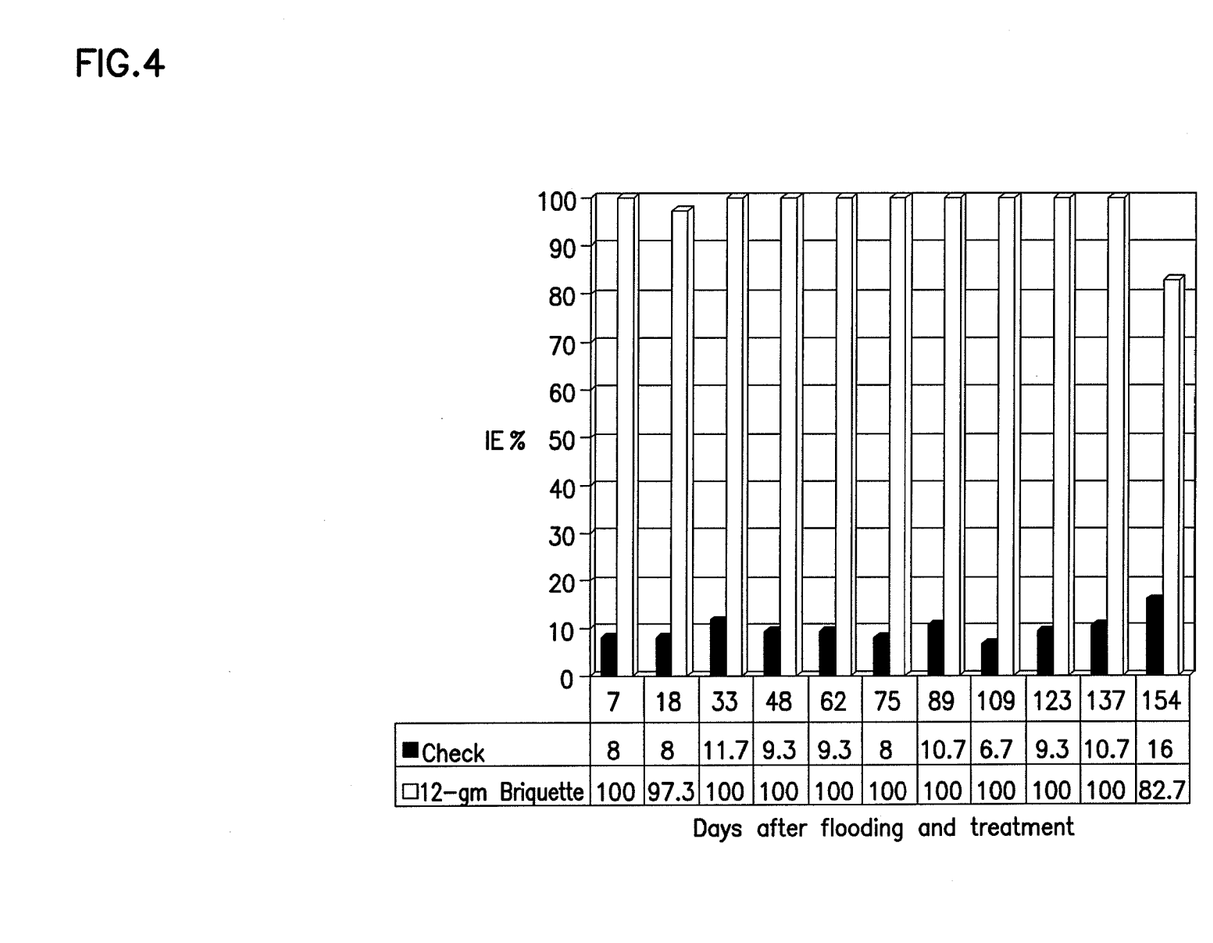
Figure 5:
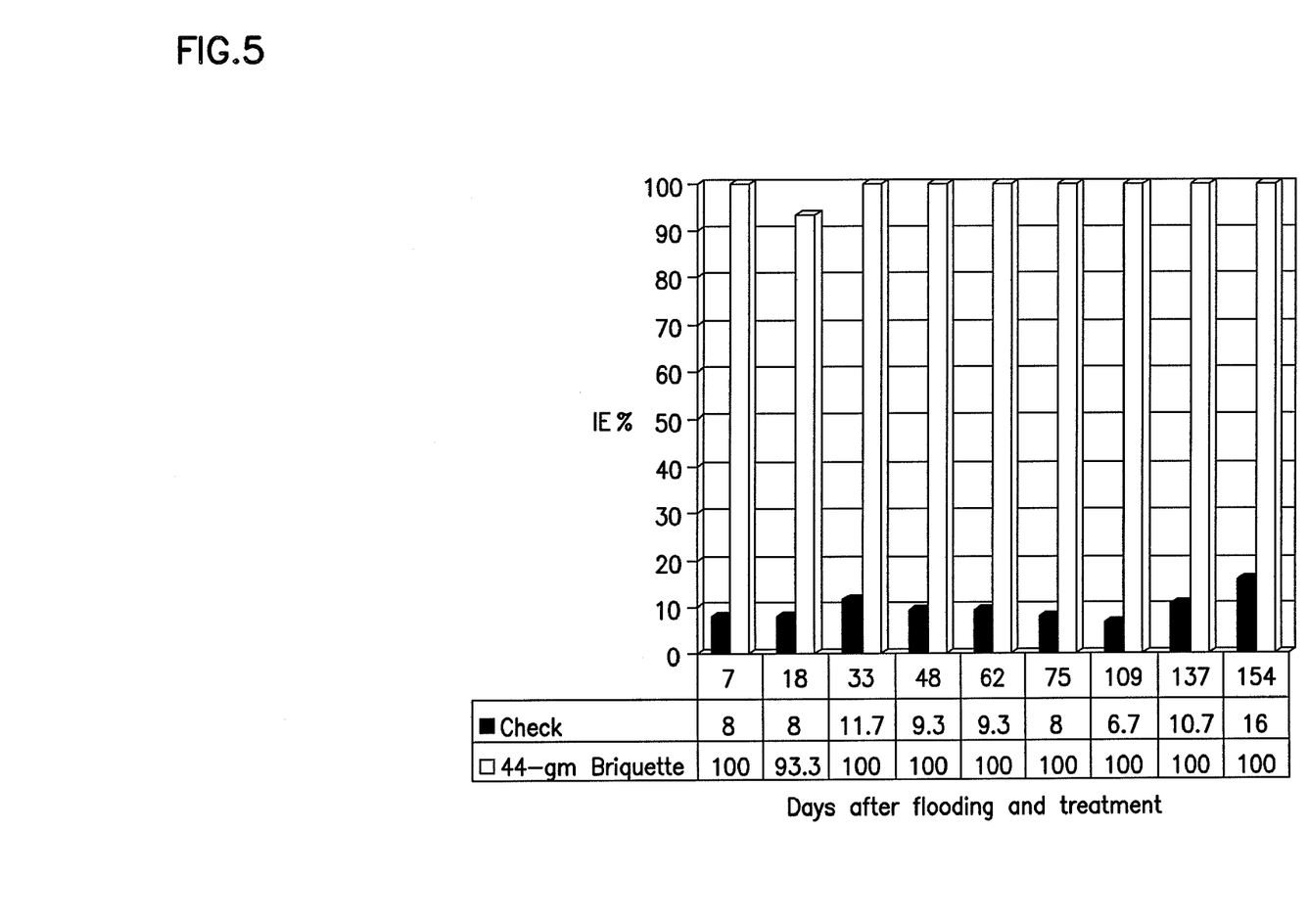
Figure 6:
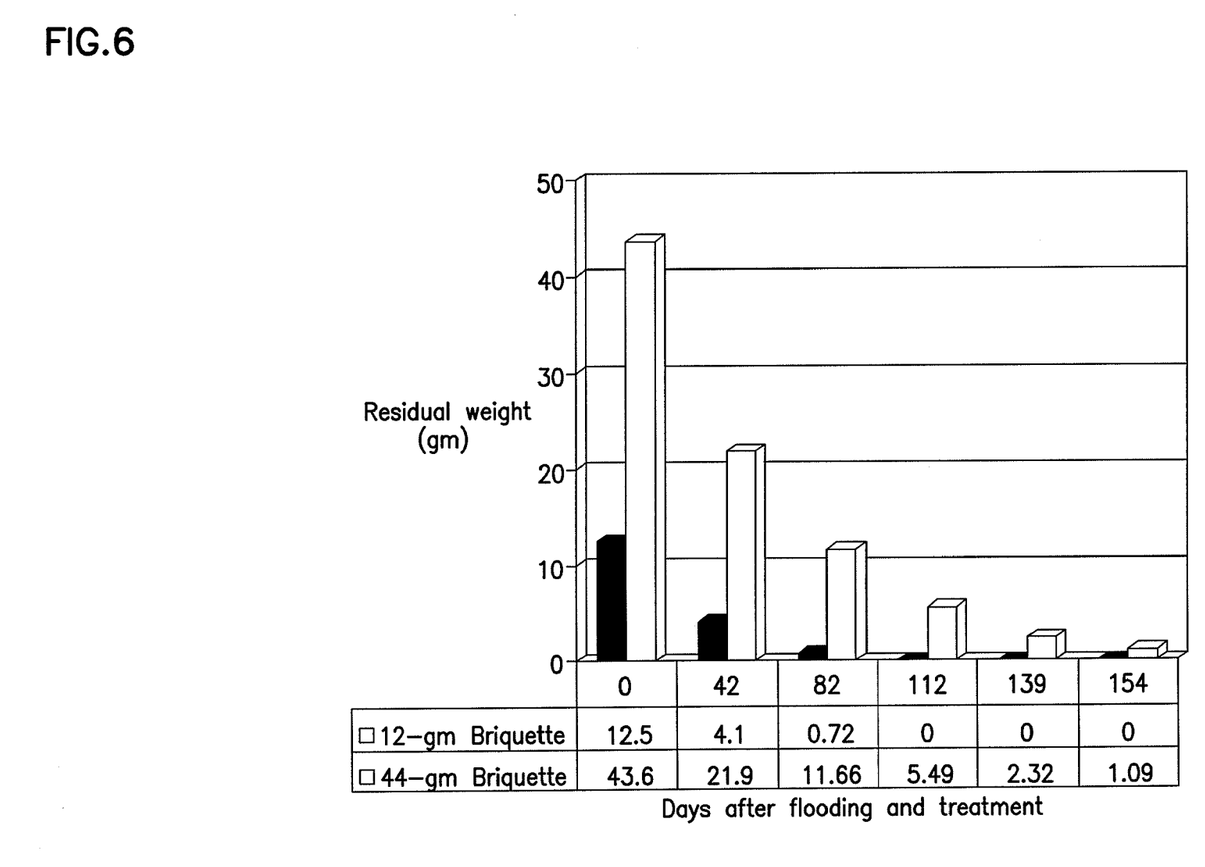
FIG. 6 shows the residual amount of briquette embodiment of the invention in the flooded site over time.
Figure 7:
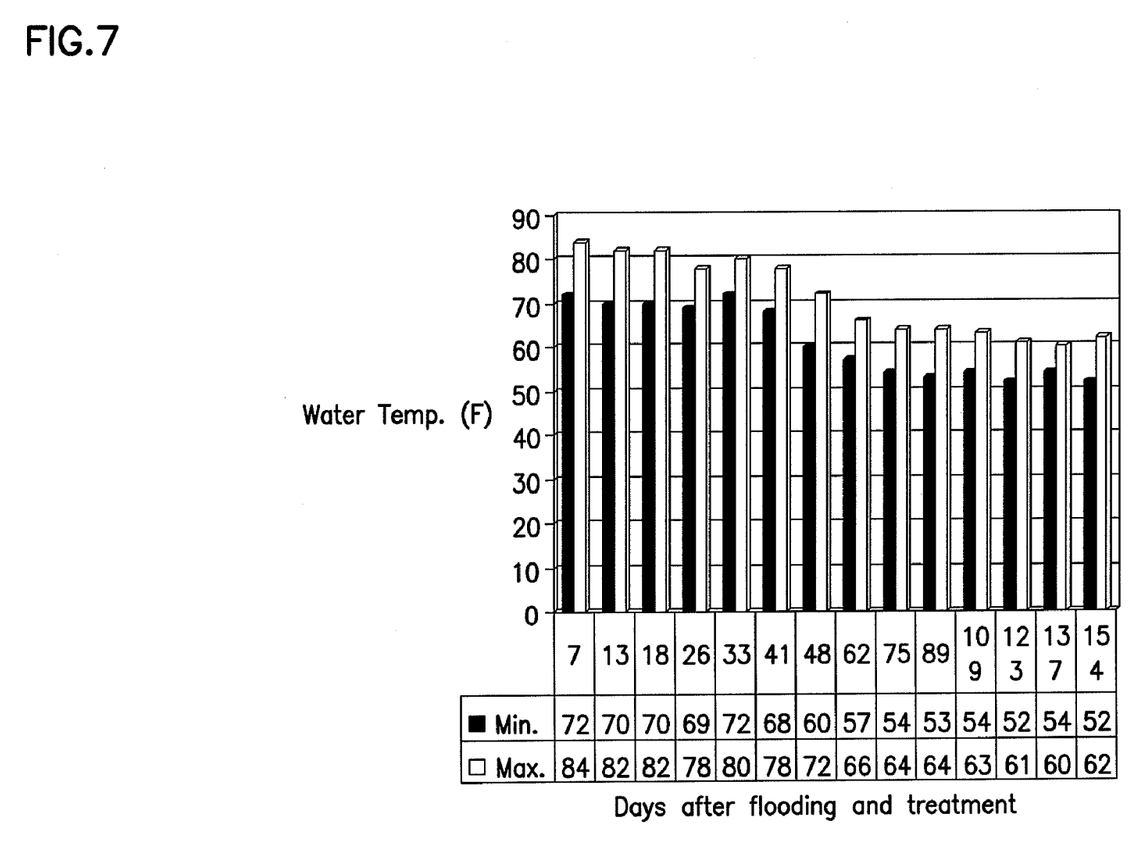
FIG. 7 shows the water temperature of the test aqueous location.

All microcosm tests were conducted under the same conditions, discussed above. FIG. 1 presents the control efficacy of Bti pellets against successive cohorts of *Aedes aegypti* larvae. FIG. 2 shows the 12 gm Bti briquette provided 97% Inhibition of Emergence (I.E.) control of *Culex quinquefasciatus* mosquitoes for 123 days and >85% control for 154 days. FIG. 3 shows the 44 gm briquette achieved >93% I.E. of *Culex quinquefasciatus* mosquito larvae for 154 days. Similarly, FIG. 4 shows the 12 gm Bti briquette gave >97% control for 137 days, and 82% control at 154 days against *Aedes aegypti* larvae. Finally, FIG. 5 presents the results of the 44 gm briquette which gave >93% I.E. of *Aedes aegypi* mosquito larvae for 154 days. FIG. 6, shows the residual amount of the 12 and 44 gram briquettes remaining over time. Lastly, FIG. 7 shows the water temperature during the test period.

The above specification, examples and data provide a basis for understanding and using the invention as is understood at this time. While many embodiments of the invention can be made, the invention resides in the claims that follow.

We claim:

1. A solid pest control unit having a mass of about 3 to 45 grams, the unit comprising a composition comprising about 30 to 90 wt.-% of a plaster matrix, the matrix comprising a plaster having a high compressive strength of at least 500 lbs, per square inch and having a hardening amount of water, and about 2 to 15 wt.-% of a polypropylene powder buoyant agent having an internal void, the void comprising about 2 to 10 wt.-% of a *Bacillus thuringiensis israelensis* particulate microbial pest control agent, wherein the unit is sufficiently hard to be distributed over large areas by mechanical means, has a surface area of about 10 to about 50,000 mm$^2$, and when immersed in an aqueous pest breeding site, the plaster matrix causes the unit to sink to the bottom of the site and release the polypropylene particulate buoyant agent to the surface, providing up to 154 days of control days of control with an effective amount of the pest control agent, wherein the unit when dry does not release the agent, and wherein the combination of polypropylene powder and the microbial pest control agent, when soaked in water for more than 24 hours, demonstrates a specific gravity of less than 1.0.

2. The solid pest control unit of claim 1 wherein the surface area of the object is about 2,000 to 30,000 $mm^2$.

3. The solid pest control unit of claim 2 wherein the surface area of the object is about 2,500 to 7,500 $mm^2$.

4. A pest control unit of claim 1 wherein the unit is a cylinder having dimensions of about 1 to 100 millimeters in diameter and about 1 to 100 millimeters in height.

5. The pest control unit of claim 1 wherein the unit is a truncated cone having dimensions of about 20 to 45 millimeters on the major diameter, about 15 to 35 millimeters on the minor diameter, and about 15 to 40 millimeters in height.

6. The pest control unit of claim 5 wherein the dimensions of the truncated cone are about 35 to 40 millimeters in the major diameter, about 30 to 35 millimeters in the minor diameter, and about 30 to 35 millimeters in height.

7. The solid pest control unit of claim 6 wherein the surface area of the solid pest control unit is about 4,000 to 7,000 $mm^2$.

* * * * *